United States Patent [19]

Mazzoleni et al.

[11] Patent Number: 5,150,608
[45] Date of Patent: Sep. 29, 1992

[54] CENTERING DEVICE FOR USE WITH BRINELL HARDNESS-MEASURING PROBE

[76] Inventors: Giancarlo Mazzoleni, 4 Logger Mill Rd., Horsham, Pa. 19044; Gordon M. Baker, 5592 Long La., Doylestown, Pa. 18901

[21] Appl. No.: 657,596

[22] Filed: Feb. 19, 1991

[51] Int. Cl.⁵ .............................................. G01N 3/48
[52] U.S. Cl. ...................................................... 73/81
[58] Field of Search .................................... 73/81-83; 356/379, 384

[56] References Cited

U.S. PATENT DOCUMENTS

| | | |
|---|---|---|
| D. 283,599 | 4/1986 | Biddle, Jr. et al. |
| D. 304,427 | 11/1989 | Biddle |
| 2,305,760 | 12/1942 | Bernhardt .............. 73/81 |
| 3,763,697 | 10/1973 | Sturm ..................... 73/81 |
| 4,945,490 | 7/1990 | Biddle, Jr. et al. |

FOREIGN PATENT DOCUMENTS

| | | | |
|---|---|---|---|
| 0042838 | 3/1982 | Japan ..................... | 73/81 |
| 467806 | 6/1937 | United Kingdom ..... | 73/81 |

OTHER PUBLICATIONS

NewAge Industries Testing Instrument Division *Technical Bulletin*, "A Major Development in Brinell Hardness Testing from Newage Industries The B.O.S.S.", 1 sheet (two-sided).

Newage Industries Inc. brochure, "Newage Brinell Scopes Improves Accuracy & Speed of Brinell Impression Measurement", 1 sheet (two-sided).

*Primary Examiner*—Robert Raevis
*Attorney, Agent, or Firm*—Panitch Schwarze Jacobs & Nadel

[57] ABSTRACT

A centering device for Brinell hardness-measuring instruments includes an alignment member positioned at the opening of the instrument providing a field of view to the optics within the instrument. A central portion of the alignment member protrudes through the instrument opening and is hemispherically configured to mate with a circular Brinell penetrator indentation in the specimen surface. The central portion of the alignment member is open to freely pass light axially through the alignment member. The alignment member is preferably spring supported within the instrument to permit the alignment member to partially retract into the instrument and the working face of the instrument to be positioned against the specimen. A switch is provided responsive to movement of the alignment member to activate a light source in the instrument.

11 Claims, 3 Drawing Sheets

CENTERING DEVICE FOR USE WITH BRINELL HARDNESS-MEASURING PROBE

FIELD OF THE INVENTION

The invention relates generally to metal hardness testing and specifically to determination of Brinell indentation diameter for metal hardness testing.

BACKGROUND OF THE INVENTION

Metal hardness is typically determined by indenting a metal specimen at a known force with a known device and measuring either the depth or diameter of the indentation. Diameter testing is most commonly referred to as Brinell testing. See ASTM E10 (10-78), incorporated herein by reference. In Brinell testing, a ball penetrator, either 5 mm or, more typically, 10 mm in diameter, is applied to a test specimen with a predetermined load to produce a generally spherical indentation in the specimen. Knowing the applied force, the Brinell hardness of the test specimen can be determined from the diameter of the indentation.

Current Brinell testing involves measuring the diameter of the indentation along orthogonal axes using either a small optical microscope with a graded reticle or an electro-optical probe device which indicates or responds to, respectively, the differences in light reflected from the specimen surrounding the indentation, the side walls of the indentation and the indentation itself. Each type of instrument can be positioned over and against a specimen. Each instrument generates a magnified image of the underlying specimen surface. The operator moves the instrument to try to center the instrument over the center of the indentation. Each instrument also typically employs light focused or otherwise directed through the instrument so that when the central axis of the instrument is perpendicular to the specimen surface, the light also strikes the specimen surface beneath the instrument to illuminate that area including the indentation.

A major problem with each type of instrument is the difficulty in locating and then accurately centering the instrument with respect to the indentation. In most instances, a field of view relatively large with respect to the size of the indentation must be provided in order to permit the operator to view a sufficiently large area of the specimen surface to orient the probe with respect to the indentation. In some instances, due to a roughness of the specimen surface and/or the polish of the side walls of the indentation, the contrast between light reflected from the undisturbed surface and the indentation is relatively low, making it difficult for the operator to optically identify the indentation and center of the indentation. While the newest optical Brinell hardness-measuring electrode probes are configured to compensate for misalignment of the probe with respect to the central axis of the indentation, such misalignment between the indentation and the central optical axis of the probe can still lead to some degradation of accuracy in the diameter measurement. In addition, because a relatively large field of view is provided to the optical system to permit the operator to find the indentation, the resolution of the optical system is reduced.

It would, therefore, be desirable to provide a means and a method to simplify alignment of a Brinell hardness optical measuring probe with a Brinell indentation which simplifies the measurement procedure in a way which does not adversely affect the measurement results.

SUMMARY OF THE INVENTION

The invention is a centering device to improve a Brinell hardness-determining instrument, the instrument having an end for placement on a specimen surface to be examined and an opening through the end of the instrument providing to optics within the instrument a field of view of the specimen surface on which the end of the instrument is placed, the centering device comprising an alignment member having a central axis and two opposing axial sides, a portion of the alignment member protruding generally concentrically with respect to the central axis from one axial side of the alignment member through the opening to form a centering structure of the alignment member shaped to mate with a generally circular indentation in the specimen surface, a central portion of the alignment member further being configured to freely pass light axially through the alignment member generally around the central axis whereby the field of view of the instrument through the opening is at least substantially unblocked.

BRIEF DESCRIPTION OF THE DRAWINGS

The foregoing summary as well as the following detailed description of the presently preferred embodiment of the invention will be better understood when read in conjunction with the appended drawings. For the purpose of illustrating the invention, there is shown in the drawings an embodiment which is presently preferred. It should be understood, however, that the present invention is not limited to the particular arrangements and instrumentalities shown. In the drawings.

DETAILED DESCRIPTION OF PREFERRED EMBODIMENT

Figure 1:
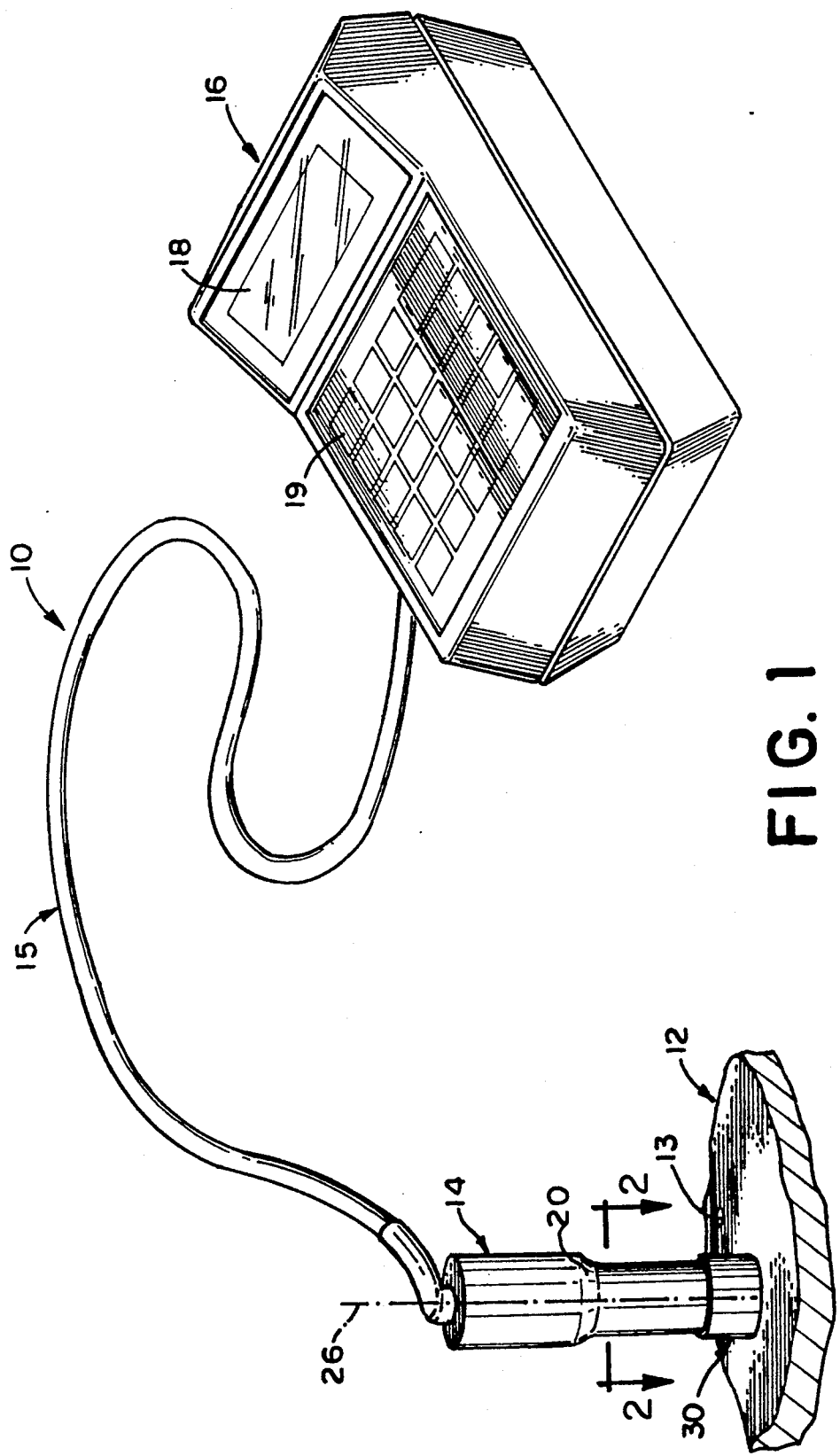
FIG. 1 depicts a portable Brinell hardness-measuring apparatus including a hand-held electro-optical probe-type instrument mounting a preferred embodiment centering device of the present invention.

Like reference numerals are used to identify the same elements in the various drawings.

FIG. 1 depicts schematically an exemplary, electro-optically configured Brinell hardness-measuring apparatus indicated generally at 10 and, in conjunction with it, a specimen 12 the hardness of which is being measured. Electro-optical Brinell hardness measuring apparatus are known and have been disclosed and discussed in a variety of U.S. patents, including for example, U.S. Pat. No. 4,945,490, which is incorporated by reference herein in its entirety, as well as in other printed, published literature. The novelty of the present invention does not reside in such conventional apparatus, per se, but rather in the centering devices to be described which are improvements to such apparatus as well as to microscope type Brinell hardness-measuring instruments, either as an aftermarket accessory or, preferably, configured into the instruments during original manufacture.

The exemplary Brinell measuring apparatus 10 in FIG. 1 includes a hand-held, electro-optical instrument or probe 14 physically and electrically coupled by appropriate cabling 15 with an associated processor 16 preferably including an optical display 18 and keyboard 19. The instrument or probe 14 includes an outer, generally tubular housing 20 which typically contains light source and photoresponsive components (indicated collectively, diagrammatically and in phantom at 22 in FIG. 3). These respectively illuminate and respond to light reflected from the underlying specimen 12. Power is typically supplied to a light source in the probe 14 through the cabling 15 from the processor 16 while one or more signals from the photoresponsive component(s) are returned from the probe 14 to the processor 16 through the cabling 15 for processing.

The probe 14 has one end 24 with a preferably circular (see FIG. 2) opening 25 therethrough, preferably centrally located with respect to the housing 20 and end 24. The end 24 is planar for butting the end against a specimen planar surface. The opening 25 provides a field of view to the conventional light source and photoresponsive components 22 of the probe 14 of the surface of the specimen 12 on which the end 24 of the probe 14 is placed. Preferably the optic components of the probe 14 have a central optical axis which, in the case of the probe 14 of the present example is preferably coincident with the central axis of the outer tubular housing 20 and center of opening 25. This central, coincident axis is indicated diagrammatically at 26 in the figures. Mounted at the one working end 24 of the probe 14 is a centering device of the present invention, which is indicated generally at 30 in the figures.

Figure 2:
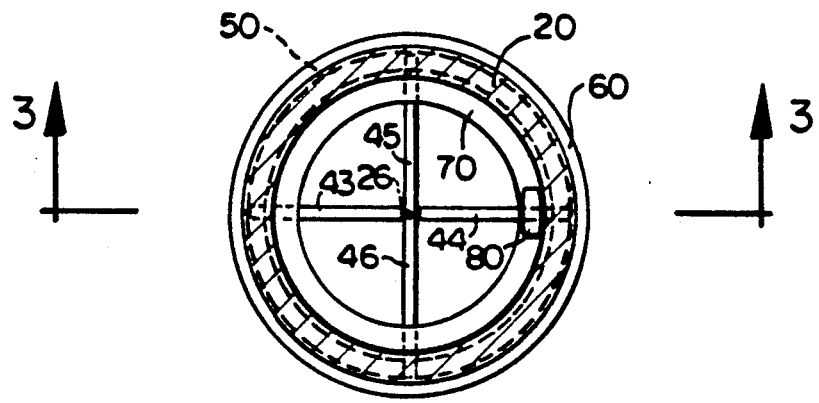
FIG. 2 is a diagrammatic cross-sectional view of the probe taken along the lines 2—2 of FIG. 1.
Figure 3:
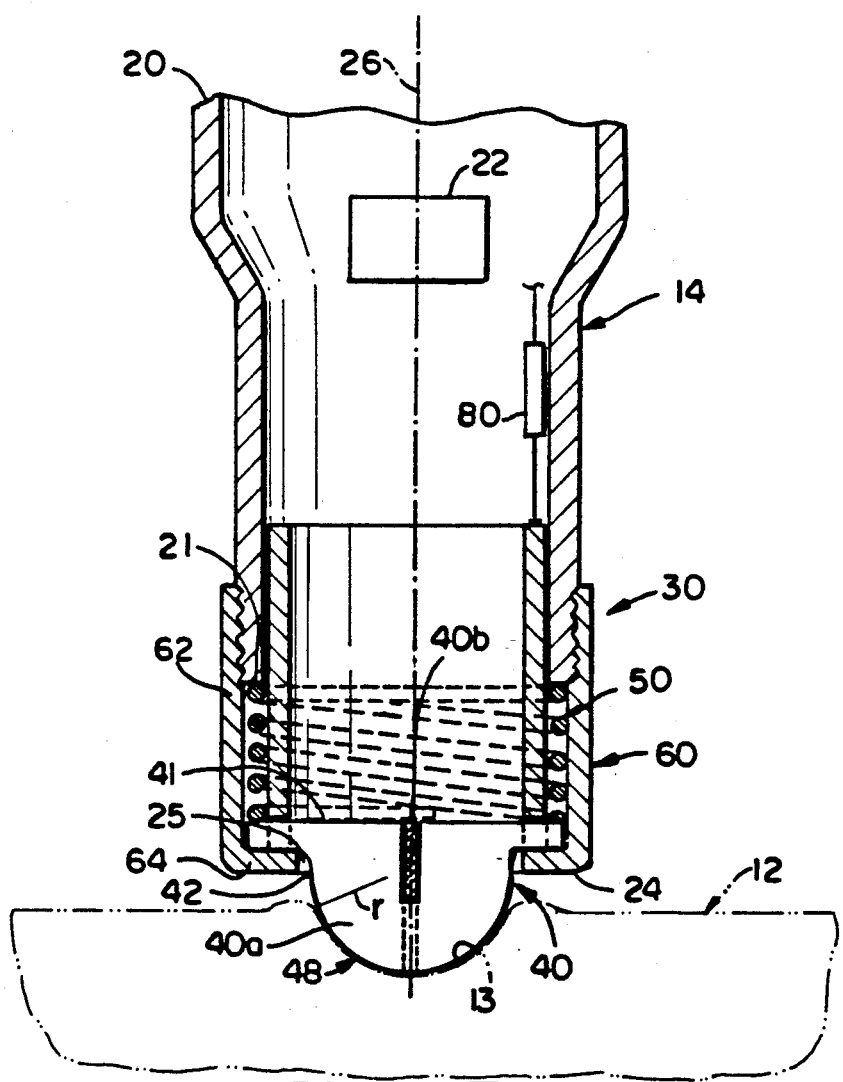
FIG. 3 is a cross-sectional view of the probe taken along the lines 3—3 of FIG. 2.

Referring to FIGS. 2 and 3, the basic centering device 30 preferably comprises an alignment member, indicated generally at 40, and biasing means, indicated generally at 50, A coupling means, indicated generally at 60, may further be provided for retrofitting the centering device 30 to existing probes.

Referring specifically to FIG. 3, the preferred alignment member 30 has a central axis which is at least generally coincident with the central axis 26 of the optical probe 14. The centering device 30 has two axial sides, indicated generally at 41 and 42. The centering device 30 is preferably formed by two interfitted pieces 40a, 40b defining four arms 43, 44, 45 and 46 extending radially with respect to the central axis 26 of the centering device, as represented by a coincident axis 26 in the figures. Each of the pieces and each of the arms 43-46 is perpendicular to its adjoining neighbor. This is best seen in FIG. 2. Preferably, a central portion of each of the arms 43-46 extends radially away from the axis 26 with a radius of curvature "r" forming a convexly curved outer surface. After curving through an arc of approximately ninety degrees, each arm 43-46 thereafter extends radially outwardly from the central axis 26 in a direction generally perpendicular to said axis 26. Collectively, the radiused portions of the arms 43-46 form a centering structure protruding generally concentrically with respect to the central axis 26 on one axial side 42 of the alignment member 40 through the opening 25. As is indicated in FIG. 2, the arms 43-46 leave open a major proportion of the central area of the alignment member 40, which is circumscribed by the opening 25 in end 24 of the probe 14. This open central area permits light to pass freely between the optical component(s) within the probe, indicated generally at 22 in FIG. 3, and the opposing specimen 12, whereby the field of view of the optics 22 of the probe 14 through opening 25 is at least substantially unblocked, permitting the probe 14 to make/take optical readings axially through the alignment member 40.

The alignment member 40 is biased away from the proximal end 24 of the probe 14 by biasing the means. Preferably the biasing means is provided in the form of a coil spring also identified by the same reference number 50. The alignment member 40 and biasing means spring 50 are held concentrically with respect to one another and the central axis 26 by the coupling means 60, which is preferably provided in the described embodiment by a generally tubular collar member, indicated by the same reference number 60. Coupling means/member 60 preferably includes a generally cylindrical wall 62, concentric with the central axis 26, preferably threaded on an inner circumferential side thereof at one end to engage threading which has been provided on the lower open end of the outer tubular housing 20 of the probe 14. An annular flange 64 extends radially inwardly from the cylindrical wall 62 at the end of the wall spaced farthest from the optical probe 14 and defines the surface of the one end 24 and the opening 25 therethrough. The flange 64 retains the alignment member 40 and biasing means spring 50 within the probe 14. In this way, the coupling means/member 60 couples the alignment member 40 and biasing means spring 50 with the probe 14 such that the central axis of the alignment member 40 is generally coincident with the central axis 26 of the probe and the alignment member 40 is supported for movement in the axial direction with respect to the probe 14 biased away from the probe 14 by the biasing means spring 50.

The alignment member 40 may be formed, for example, by a pair of planar, stamped metal pieces which are slotted and interfitted perpendicularly at their centers to form the four radiating arms 43-46. It is envisioned each arm might be approximately fifteen mils thick and at least about one hundred twenty-five mils high with a radius of curvature "r" of 5 mm to mate with a circular indentation 13 in the surface of specimen 12 formed by a 10 mm diameter circular Brinell penetrator. Where a circular penetrator of a different diameter is employed, the radii of the curvature of arms 43-46 are adjusted accordingly.

Preferably, the centering device 30 further comprises a ring member 70 sized for slidable movement within the outer tubular housing 20 of the probe 14. Ring member 70 assists in keeping the biasing means spring 50 in concentric position and in keeping the alignment member 40 from pitching severely, causing it to possibly dislodge from the probe 14 or jam within the probe 14. Preferably, too, the alignment member 40 is coupled with the ring member 70 in a way which retards relative movement between the alignment member 40 and the ring in member 70, such as, for example, by the provision of slots at the lower end of the ring member 70 which receive each of the arms 43-46. Preferably, the arms 43-46 of the alignment member 40 are fixedly secured with the ring member 70 by soldering, spot welding, adhesive, frictional engagement or other means suitable for the materials selected to form an integral structure, which itself constitutes an alternate embodiment alignment member of the present invention.

It is further contemplated that the centering device 30 of the present invention will include switch means, indicated diagrammatically at 80, which is configured and located to respond to the depression of the probe 14 against the specimen 12 after receipt of the centering structure 48 in a Brinell penetrator indentation, such as indentation 13 illustrated in FIG. 3. The switch means 80 will be discussed further with respect to the following discussion of the operation of the centering device 30 with the probe 14.

After installing the centering device 30 at the optical, working end 24 of the probe 14, the centering device 30 is positioned by the operator against the specimen 12 bearing one or more of the Brinell indentations 13. The operator moves the probe 14 across the surface of the specimen 12 with the alignment member 40 contacting and running across the surface until the protruding centering structure 48 is caught in an indentation 13. Once the centering structure is caught in the indentation 13, the annular flange portion 64 of the coupling member 60 is pressed against the facing surface of the specimen 12 to automatically center and vertically align and space the probe 14 with respect to that surface. In this way, the probe 14 can be virtually automatically aligned with respect to the indentation 13 in a manner which eliminates the incremental movement required of prior instruments without the present centering device.

Preferably, the switch means 80 is one that will respond to the upward movement of the alignment member 40, for example, a switch means responsive to the movement of the ring member 70 or alignment member 40 away from a position occupied by either of those members before alignment is achieved and the probe depressed against the specimen surface. Such a switching means can include, for example, but is not limited to a throw switch, a momentary contact switch, a Hall effect or other proximity switch, a photoresponsive element exposed (or covered) by movement of the ring member 70, a pressure switch responsive to the change in biasing force of the biasing means spring 50, a contact switch formed by overlapping contacting conductive portions of the ring 70 and housing 20 or alignment member 40 and coupling means/member 60 or any number of other possible switching means, any of which could be selected and incorporated into the centering device 30 (and/or the probe 14) in any of a variety of ways. The processor 16 of the apparatus 10 can be configured to respond to such a signal to begin a series of automatic measurements and computations leading to the derivation of a Brinell hardness value assigned to the specimen 12 as a result of automatic diametral measurements of the indentation 13.

The centering devices of the present invention can equally be incorporated into microscope-type Brinell hardness-determining instruments. The centering device would again be incorporated into the optical working end of the scope, either during original design and manufacture of the scope or, in at least some cases, by being retrofitted into a conventional instrument. Scope-type instruments are typically provided with a reticle having a single diametral axis which is gradiated numerically from the left to right. Typically, the operator attempts to align the reticle with the Brinell penetrator indentation in a way in which the operator can read off the diameters of the indentation. This typically requires considerable incremental movement of the scope to properly position the reticle with respect to the indentation.

Figure 4:
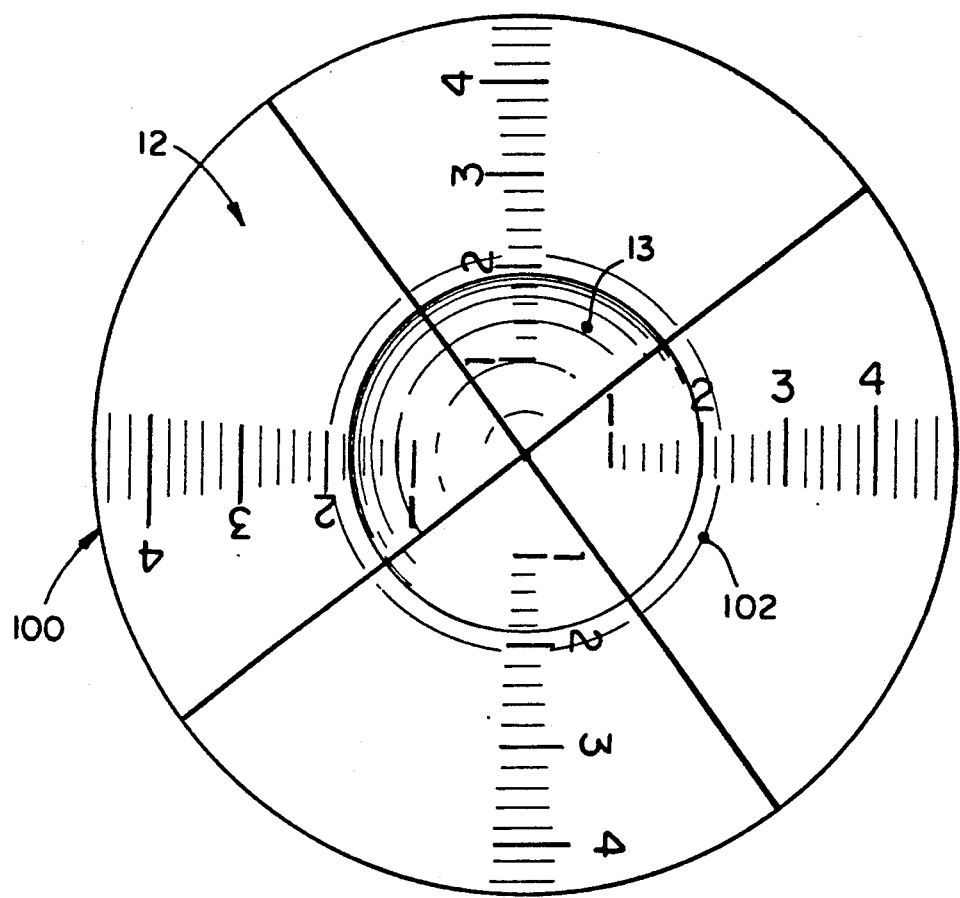
FIG. 4 depicts diagrammatically a preferred reticle used with a Brinell hardness-determining microscope equipped with the centering device of the present invention.

The centering device of the present invention greatly simplifies not only the alignment process but the subsequent measurement process of such scopes. Since the centering structure of the centering device of the present invention aligns the optical axis of the scope with the center of the indentation receiving the centering structure, a cross-hair type reticle like reticle 100 100 in FIG. 4 can be provided inscribed with diametral as opposed to radial values along each radial arm ("1", "2", "3", "4" mm, etc.) of the cross hair so that the operator can tell, at a glance, by simply reading the numbers from the gradiated scale, the diameter(s) of the indentation regardless of the rotational position of the scope. In addition, because the centering device of the present invention accurately aligns a scope on which it is installed concentrically with an indentation to be measured, it permits the possibility of providing GO/-NO-GO type reticles for product grading. Such a reticle would be scored or otherwise marked in some way, for example, to provide a circle like circle 102, or segments of such a circle, to indicate a maximum indentation diameter corresponding to a minimum specified hardness. Thus, in FIG. 4 indentation 13 lies within circle 102 indicating the sample is sufficiently hard. Where a hardness range is to be verified, a pair of GO/-NO-GO circles or the like could be provided, one to indicate a minimum diameter permitted by a maximum hardness tolerance for a specific material and a maximum diameter marking for a minimum hardness tolerance permitted for the material by the specification. The operator would simply verify that the rim of the indentation 13 lies within the two sets of marking to assure that the sample lies within the specified hardness tolerance range. In addition, many Brinell hardness-testing scopes are provided with removable eye pieces which contain the reticle. Thus, such instrument could easily be modified to measure different hardnesses or to measure indentation diameter to determine a hardness simply by substituting a different eye piece. In addition, in those existing scopes in which it would be difficult to retrofit a centering device of the present invention without altering the spacing of the original working end of the scope from its optics, it would be possible to add a centering device to the existing working end of such a scope and provide a new eye piece, the optics of which are altered to take into account the increased spacing provided between the optics from the addition of the centering device to the working end of the scope.

While a preferred centering device for an electro-optically configured Brinell hardness determining instrument has been described and variations to the instrument and preferred device suggested, still other variations thereto are clearly possible and would be known to others of ordinary skill in this art. Accordingly, the invention is not limited to the precise embodiment disclosed but rather is intended to cover any modifications which are within the scope and spirit of the invention, as defined by the appended claims.

We claim:

1. A centering device to improve a Brinell hardness-determining instrument, the instrument having one end configured for placement on a specimen surface to be examined and an opening through the one end providing to optics within the instrument a field of view of the specimen surface on which the one end of the instrument is placed, the centering device comprising:

an alignment member having a central axis and two opposing axial sides, a portion of the alignment member protruding generally concentrically with respect to the central axis from one axial side of the alignment member through the opening to form a centering structure of the alignment member shaped to mate with a generally circular indentation in the specimen surface, a central portion of the alignment member further being configured to freely pass light axially through the alignment member generally around the central axis whereby the field of view of the instrument through the opening is at least substantially unblocked.

2. The centering device of claim 1 further comprising:

biasing means concentrically positioned with respect to the alignment member and the instrument for biasing the one side of the alignment member and the centering structure axially away from the instrument through the opening.

3. The centering device of claim 2 further comprising:

coupling means for coupling the alignment member and the biasing means with the instrument such that the central axis of the alignment member is at least generally coincident with an optical axis of the instrument and the alignment member is supported for movement in the axial direction biased away from the instrument by the biasing means.

4. The centering device of claim 1 wherein the alignment member includes at least three arms extending radially with respect to the central axis, each of the arms protruding generally axially on the one side of the alignment member so as to collectively define at least part of the centering structure of the alignment member protruding from the one end of the instrument through the opening.

5. The device of claim 4 wherein the one axial side of each of the arms is radially curved.

6. The device of claim 4 wherein the alignment member has a total of four arms, each arm being perpendicularly positioned with respect to each adjoining arm.

7. The device of claim 6 wherein the alignment member further comprises a tubular member having openings extending radially therethrough receiving each of the arms, the tubular member being positioned concentrically with respect to the central axis.

8. The device of claim 1 further comprising switch means for responding to the alignment member when the one end of the instrument is moved towards the sample after mating of the centering structure with Brinell indentation.

9. The centering device of claim 1 in combination with a reticle for a Brinell hardness-determining microscope, the reticle being marked with at least a pair of perpendicular gradiated axes.

10. The centering device of claim 1 in combination with a reticle for a Brinell hardness-determining microscope, the reticle being marked with a gradiated axis bearing numerals indicating diameters along the axis.

11. The centering device of claim 1 in combination with a reticle for a Brinell hardness-determining microscope, the reticle being marked with single diametral measurement to indicate a specific Brinell hardness diameter for GO/NO-GO hardness testing.

* * * * *